United States Patent
Wang

(10) Patent No.: US 11,045,088 B2
(45) Date of Patent: Jun. 29, 2021

(54) THROUGH FOCUS RETINAL IMAGE CAPTURING

(71) Applicant: Welch Allyn, Inc., Skaneateles Falls, NY (US)

(72) Inventor: Ynjiun Paul Wang, Cupertino, CA (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 14/633,601

(22) Filed: Feb. 27, 2015

(65) Prior Publication Data

US 2016/0249804 A1 Sep. 1, 2016

(51) Int. Cl.
*A61B 3/12* (2006.01)
*A61B 3/00* (2006.01)
*A61B 3/15* (2006.01)

(52) U.S. Cl.
CPC .............. *A61B 3/12* (2013.01); *A61B 3/0025* (2013.01); *A61B 3/0041* (2013.01); *A61B 3/152* (2013.01)

(58) Field of Classification Search
CPC ....... A61B 3/165; A61B 3/152; A61B 3/1233; A61B 3/1241; A61B 3/0041; A61B 5/14555; A61B 3/0025
USPC .................... 351/200, 208, 210, 224; 348/78
See application file for complete search history.

(56) References Cited

U.S. PATENT DOCUMENTS

| | | |
|---|---|---|
| 5,048,946 A | 9/1991 | Sklar et al. |
| 5,557,350 A | 9/1996 | Yano |
| 5,599,276 A | 2/1997 | Hauptli et al. |
| 5,703,621 A | 12/1997 | Martin et al. |
| 5,713,047 A | 1/1998 | Kohayakawa |
| 5,776,060 A | 7/1998 | Smith et al. |
| 5,784,148 A | 7/1998 | Heacock |
| 5,943,116 A | 8/1999 | Zeimer |
| 6,000,799 A | 12/1999 | Van de Velde |
| 6,011,585 A | 1/2000 | Anderson |

(Continued)

FOREIGN PATENT DOCUMENTS

| | | |
|---|---|---|
| CN | 1704017 A | 12/2005 |
| CN | 102324014 A | 1/2012 |

(Continued)

OTHER PUBLICATIONS

Mayer et al. Wavelet denoising of multiframe optical coherence tomography data; Mar. 1, 2012 / vol. 3, No. 3 / Biomedical Optics Express.*

(Continued)

*Primary Examiner* — Travis S Fissel
(74) *Attorney, Agent, or Firm* — Merchant & Gould P.C.

(57) ABSTRACT

An apparatus for producing a non-mydriatic fundus image is disclosed. The apparatus can include a processor and memory, as well as an illumination component and a camera with a variable focus lens. The apparatus can be configured to adjust the focus of the lens to a plurality of different diopter ranges and capture at least one image at each of the plurality of different diopter ranges. A method for capturing a non-mydriatic image of a fundus is also disclosed. The method can include setting a depth of field, dividing the depth of field into a plurality of zones, adjusting a variable focus lens of a camera to focus on each of the plurality of zones, and capturing at least one image at each of the plurality of zones.

10 Claims, 7 Drawing Sheets

(56) References Cited

U.S. PATENT DOCUMENTS

| | | | |
|---|---|---|---|
| 6,120,461 A | 9/2000 | Smyth | |
| 6,296,358 B1* | 10/2001 | Cornsweet | A61B 3/156 |
| | | | 351/206 |
| 6,301,440 B1 | 10/2001 | Bolle et al. | |
| 6,307,526 B1 | 10/2001 | Mann | |
| 6,309,070 B1 | 10/2001 | Svetliza et al. | |
| 6,325,511 B1 | 12/2001 | Mizouchi | |
| 6,350,031 B1 | 2/2002 | Lashkari et al. | |
| 6,556,853 B1 | 4/2003 | Cabib et al. | |
| 6,666,857 B2 | 12/2003 | Smith | |
| 7,134,754 B2 | 11/2006 | Kerr et al. | |
| 7,264,355 B2 | 9/2007 | Rathjen | |
| 7,284,859 B2 | 10/2007 | Ferguson | |
| 7,311,400 B2 | 12/2007 | Wakil et al. | |
| 7,364,297 B2 | 4/2008 | Goldfain et al. | |
| 7,377,643 B1 | 5/2008 | Chock et al. | |
| 7,380,938 B2 | 6/2008 | Chmielewski, Jr. et al. | |
| 7,387,384 B2 | 6/2008 | Heine et al. | |
| 7,404,640 B2 | 7/2008 | Ferguson et al. | |
| 7,470,024 B2 | 12/2008 | Chinaglia et al. | |
| 7,488,294 B2 | 2/2009 | Torch | |
| 7,502,639 B2 | 3/2009 | Kerr | |
| 7,568,628 B2 | 8/2009 | Wang et al. | |
| 7,611,060 B2 | 11/2009 | Wang et al. | |
| 7,621,636 B2 | 11/2009 | Su et al. | |
| 7,784,940 B2 | 8/2010 | Goldfain et al. | |
| 7,809,160 B2 | 10/2010 | Vertegaal et al. | |
| 7,871,164 B2 | 1/2011 | Luther et al. | |
| 7,926,945 B2 | 4/2011 | Dick et al. | |
| 7,963,653 B1 | 6/2011 | Ellman | |
| 7,976,162 B2 | 7/2011 | Flitcroft | |
| 8,109,634 B2 | 2/2012 | Gil | |
| 8,109,635 B2 | 2/2012 | Anon et al. | |
| 8,347,106 B2 | 1/2013 | Tsuria et al. | |
| 8,366,270 B2 | 2/2013 | Pujol Ramo et al. | |
| 8,388,523 B2 | 3/2013 | Vivenzio et al. | |
| 8,444,269 B1 | 5/2013 | Ellman | |
| 8,488,895 B2 | 7/2013 | Muller et al. | |
| 8,534,837 B2 | 9/2013 | Sayeram et al. | |
| 8,577,644 B1 | 11/2013 | Ksondzyk et al. | |
| 8,585,203 B2 | 11/2013 | Aikawa et al. | |
| 8,620,048 B2 | 12/2013 | Nakano et al. | |
| 8,649,008 B2 | 2/2014 | Kashani et al. | |
| 8,696,122 B2 | 4/2014 | Hammer et al. | |
| 8,714,743 B2 | 5/2014 | Verdooner | |
| 8,879,813 B1 | 11/2014 | Solanki et al. | |
| 9,204,790 B2 | 12/2015 | Wada et al. | |
| 9,211,064 B2 | 12/2015 | Wang | |
| 9,237,847 B2 | 1/2016 | Wang et al. | |
| 9,398,851 B2 | 7/2016 | Anand et al. | |
| 9,462,945 B1 | 10/2016 | Barriga et al. | |
| 9,498,126 B2 | 11/2016 | Wang | |
| 9,757,031 B2 | 9/2017 | Wang et al. | |
| 9,901,242 B2 | 2/2018 | Cheng et al. | |
| 9,918,629 B2 | 3/2018 | Wang | |
| 10,136,804 B2 | 11/2018 | Wang et al. | |
| 10,154,782 B2 | 12/2018 | Farchione et al. | |
| 10,159,409 B2 | 12/2018 | Wang et al. | |
| 10,335,029 B2 | 7/2019 | Wang et al. | |
| 10,376,141 B2 | 8/2019 | Wang | |
| 10,413,179 B2 | 9/2019 | Wang | |
| 10,413,180 B1 | 9/2019 | Barriga et al. | |
| 2002/0052551 A1 | 5/2002 | Sinclair et al. | |
| 2002/0101568 A1 | 8/2002 | Eberl et al. | |
| 2003/0009155 A1 | 1/2003 | Pawlowski et al. | |
| 2003/0071970 A1 | 4/2003 | Donnerhacke et al. | |
| 2003/0163031 A1* | 8/2003 | Madden | G06F 19/324 |
| | | | 600/300 |
| 2003/0208125 A1 | 11/2003 | Watkins | |
| 2004/0258285 A1 | 12/2004 | Hansen et al. | |
| 2005/0012899 A1* | 1/2005 | Ferguson | A61B 3/1025 |
| | | | 351/221 |
| 2005/0043588 A1 | 2/2005 | Tsai | |
| 2005/0110949 A1 | 5/2005 | Goldfain | |
| 2005/0254008 A1 | 11/2005 | Ferguson et al. | |
| 2006/0113386 A1 | 6/2006 | Olmstead | |
| 2006/0119858 A1 | 6/2006 | Knighton et al. | |
| 2006/0147095 A1 | 7/2006 | Usher et al. | |
| 2006/0159367 A1 | 7/2006 | Zeineh et al. | |
| 2006/0202036 A1 | 9/2006 | Wang et al. | |
| 2006/0202038 A1 | 9/2006 | Wang et al. | |
| 2006/0268231 A1 | 11/2006 | Gil et al. | |
| 2007/0030450 A1 | 2/2007 | Liang et al. | |
| 2007/0174152 A1 | 7/2007 | Bjornberg et al. | |
| 2007/0188706 A1 | 8/2007 | Pearson et al. | |
| 2008/0084538 A1* | 4/2008 | Maeda | A61B 3/1241 |
| | | | 351/206 |
| 2008/0165322 A1 | 7/2008 | Su et al. | |
| 2008/0231803 A1 | 9/2008 | Feldon et al. | |
| 2008/0316426 A1 | 12/2008 | Shibata et al. | |
| 2009/0096885 A1 | 4/2009 | Robinson et al. | |
| 2009/0225277 A1 | 9/2009 | Gil | |
| 2009/0275929 A1 | 11/2009 | Zickler | |
| 2009/0316115 A1 | 12/2009 | Itoh et al. | |
| 2009/0323022 A1 | 12/2009 | Uchida | |
| 2009/0323023 A1 | 12/2009 | Kogawa et al. | |
| 2010/0007848 A1 | 1/2010 | Murata | |
| 2010/0007849 A1 | 1/2010 | Liesfeld et al. | |
| 2010/0014052 A1 | 1/2010 | Koschmieder et al. | |
| 2010/0085538 A1 | 4/2010 | Masaki et al. | |
| 2010/0110375 A1 | 5/2010 | Nishio et al. | |
| 2010/0149489 A1 | 6/2010 | Kikawa et al. | |
| 2010/0208961 A1 | 8/2010 | Zahniser | |
| 2010/0238402 A1 | 9/2010 | Itoh et al. | |
| 2011/0001927 A1 | 1/2011 | Kasper | |
| 2011/0028513 A1* | 2/2011 | Zhuo | A61K 31/4164 |
| | | | 514/300 |
| 2011/0043756 A1 | 2/2011 | Kahn et al. | |
| 2011/0169935 A1 | 7/2011 | Henriksen | |
| 2011/0234977 A1* | 9/2011 | Verdooner | A61B 3/102 |
| | | | 351/207 |
| 2011/0242306 A1 | 10/2011 | Bressler et al. | |
| 2011/0261184 A1 | 10/2011 | Mason et al. | |
| 2011/0299034 A1 | 12/2011 | Walsh et al. | |
| 2011/0299036 A1 | 12/2011 | Goldenholz | |
| 2012/0002167 A1 | 1/2012 | Kondoh | |
| 2012/0033227 A1* | 2/2012 | Bower | A61B 3/102 |
| | | | 356/479 |
| 2012/0044456 A1 | 2/2012 | Hayashi | |
| 2012/0050677 A1 | 3/2012 | Ohban | |
| 2012/0121158 A1 | 5/2012 | Sekine | |
| 2012/0147327 A1 | 6/2012 | Shikaumi et al. | |
| 2012/0169995 A1 | 7/2012 | Mohr et al. | |
| 2012/0200690 A1 | 8/2012 | Beasley | |
| 2012/0213423 A1* | 8/2012 | Xu | A61B 5/0073 |
| | | | 382/131 |
| 2012/0218301 A1 | 8/2012 | Miller | |
| 2012/0229617 A1* | 9/2012 | Yates | A61B 3/156 |
| | | | 348/78 |
| 2012/0229764 A1 | 9/2012 | Tomatsu et al. | |
| 2012/0248196 A1 | 10/2012 | Wang | |
| 2012/0249956 A1 | 10/2012 | Narasimha-Iyer et al. | |
| 2012/0257163 A1 | 10/2012 | Dyer et al. | |
| 2012/0281874 A1 | 11/2012 | Lure | |
| 2012/0287255 A1 | 11/2012 | Ignatovich et al. | |
| 2012/0320340 A1 | 12/2012 | Coleman, III | |
| 2013/0002711 A1 | 1/2013 | Sakagawa | |
| 2013/0010260 A1 | 1/2013 | Tumlinson et al. | |
| 2013/0016320 A1 | 1/2013 | Naba | |
| 2013/0028484 A1 | 1/2013 | Wada et al. | |
| 2013/0033593 A1 | 2/2013 | Chinnock et al. | |
| 2013/0057828 A1 | 3/2013 | de Smet | |
| 2013/0063698 A1 | 3/2013 | Akiba et al. | |
| 2013/0128223 A1 | 5/2013 | Wood et al. | |
| 2013/0162950 A1 | 6/2013 | Umekawa | |
| 2013/0169934 A1 | 7/2013 | Verdooner | |
| 2013/0176533 A1 | 7/2013 | Raffle et al. | |
| 2013/0194548 A1 | 8/2013 | Francis | |
| 2013/0201449 A1* | 8/2013 | Walsh | A61B 3/1005 |
| | | | 351/206 |
| 2013/0208241 A1 | 8/2013 | Lawson et al. | |
| 2013/0211285 A1 | 8/2013 | Fuller et al. | |
| 2013/0215387 A1 | 8/2013 | Makihira et al. | |
| 2013/0222763 A1 | 8/2013 | Bublitz et al. | |

(56) References Cited

U.S. PATENT DOCUMENTS

| | | | |
|---|---|---|---|
| 2013/0229622 A1 | 9/2013 | Murase | |
| 2013/0234930 A1 | 9/2013 | Palacios Goerger | |
| 2013/0250237 A1 | 9/2013 | Ueno | |
| 2013/0250242 A1* | 9/2013 | Cheng | A61B 3/14 351/207 |
| 2013/0301004 A1 | 11/2013 | Kahn et al. | |
| 2014/0022270 A1 | 1/2014 | Rice-Jones | |
| 2014/0055745 A1 | 2/2014 | Sato et al. | |
| 2014/0104573 A1 | 4/2014 | Iwanaga | |
| 2014/0111773 A1 | 4/2014 | Itoh | |
| 2014/0118693 A1 | 5/2014 | Matsuoka | |
| 2014/0118697 A1 | 5/2014 | Tanaka et al. | |
| 2014/0132926 A1 | 5/2014 | Hara | |
| 2014/0180081 A1 | 6/2014 | Verdooner | |
| 2014/0192320 A1 | 7/2014 | Tsao | |
| 2014/0198298 A1 | 7/2014 | Cheng et al. | |
| 2014/0204340 A1 | 7/2014 | Verdooner | |
| 2014/0204341 A1 | 7/2014 | Murase | |
| 2014/0211162 A1 | 7/2014 | Matsuoka et al. | |
| 2014/0267668 A1* | 9/2014 | Ignatovich | A61B 3/125 348/78 |
| 2014/0268046 A1 | 9/2014 | Narasimha-Iyer et al. | |
| 2014/0307228 A1 | 10/2014 | Ohban | |
| 2014/0330352 A1 | 11/2014 | Luttrull et al. | |
| 2015/0002811 A1 | 1/2015 | Ota | |
| 2015/0009357 A1 | 1/2015 | Seibel et al. | |
| 2015/0021228 A1 | 1/2015 | Su et al. | |
| 2015/0110348 A1 | 4/2015 | Solanki et al. | |
| 2015/0150449 A1* | 6/2015 | Matsumoto | A61B 3/12 351/206 |
| 2015/0170360 A1* | 6/2015 | Fletcher | A61B 3/1225 382/128 |
| 2015/0178946 A1 | 6/2015 | Krishnaswamy et al. | |
| 2015/0272434 A1 | 10/2015 | Satake et al. | |
| 2015/0342459 A1 | 12/2015 | Robert et al. | |
| 2016/0007845 A1 | 1/2016 | Utagawa | |
| 2016/0081548 A1 | 3/2016 | Wang et al. | |
| 2016/0092721 A1 | 3/2016 | Kanagasingam et al. | |
| 2016/0120405 A1 | 5/2016 | Okuda | |
| 2016/0135678 A1 | 5/2016 | Hernandez Castanedas et al. | |
| 2016/0166141 A1 | 6/2016 | Kanagasingam et al. | |
| 2016/0188993 A1 | 6/2016 | Beato | |
| 2016/0213249 A1 | 7/2016 | Cornsweet et al. | |
| 2016/0287068 A1 | 10/2016 | Murase et al. | |
| 2016/0307341 A1 | 10/2016 | Sato et al. | |
| 2017/0020389 A1 | 1/2017 | Wang et al. | |
| 2017/0035292 A1 | 2/2017 | Wang | |
| 2017/0119241 A1 | 5/2017 | Farchione et al. | |
| 2017/0161892 A1 | 6/2017 | Tellatin et al. | |
| 2017/0172675 A1 | 6/2017 | Jarc et al. | |
| 2017/0181625 A1 | 6/2017 | Kawakami et al. | |
| 2017/0196452 A1 | 7/2017 | Wang | |
| 2017/0209044 A1 | 7/2017 | Ito et al. | |
| 2017/0239012 A1 | 8/2017 | Wood et al. | |
| 2017/0266041 A1 | 9/2017 | Kim et al. | |
| 2017/0311800 A1 | 11/2017 | Wang | |
| 2017/0316565 A1 | 11/2017 | Leahy et al. | |
| 2017/0332903 A1 | 11/2017 | Wang et al. | |
| 2018/0092530 A1 | 4/2018 | Hart et al. | |
| 2018/0140188 A1 | 5/2018 | Wang | |
| 2018/0249907 A1 | 9/2018 | Wang et al. | |
| 2018/0263486 A1 | 9/2018 | Farchione et al. | |
| 2019/0038124 A1 | 2/2019 | Wang et al. | |
| 2019/0082950 A1 | 3/2019 | Farchione et al. | |
| 2019/0269324 A1 | 9/2019 | Wang et al. | |

FOREIGN PATENT DOCUMENTS

| | | |
|---|---|---|
| CN | 102626304 A | 8/2012 |
| CN | 102917634 A | 2/2013 |
| CN | 205006859 U | 2/2016 |
| CN | 105433899 A | 3/2016 |
| CN | 205181314 U | 4/2016 |
| EP | 2 374 404 A1 | 10/2011 |
| EP | 2 425 763 A1 | 7/2012 |
| GB | 2378600 A | 12/2003 |
| JP | 2006-101943 A | 4/2006 |
| JP | 2009-172157 A | 8/2009 |
| JP | 2009-219644 A | 10/2009 |
| JP | 2010-57547 A | 3/2010 |
| JP | 2011-097992 A | 5/2011 |
| JP | 2012-213575 A | 11/2012 |
| JP | 2013-46850 A | 3/2013 |
| JP | 2013-59551 | 4/2013 |
| KR | 10-2013-0010079 | 1/2013 |
| WO | 2004/089214 A2 | 10/2004 |
| WO | 2006/016366 A2 | 2/2006 |
| WO | 2008/106802 A1 | 9/2008 |
| WO | 2010/080576 A1 | 7/2010 |
| WO | 2010/115195 A1 | 10/2010 |
| WO | 2011/029064 A1 | 3/2011 |
| WO | 2012/009702 A1 | 1/2012 |
| WO | 2012/134272 A1 | 10/2012 |
| WO | 2013/041658 A1 | 3/2013 |
| WO | 2013/082387 A1 | 6/2013 |
| WO | 2013/107464 A1 | 7/2013 |
| WO | 2014/182769 A1 | 11/2014 |
| WO | 2015/044366 A1 | 4/2015 |
| WO | 2015/100294 A1 | 7/2015 |
| WO | 2015/170947 A1 | 11/2015 |
| WO | 2016/070781 A1 | 5/2016 |
| WO | 2017223208 A1 | 12/2017 |

OTHER PUBLICATIONS

U.S. Appl. No. 14/177,594, filed Feb. 11, 2014.

International Search Report and Written Opinion in PCT/US2016/015653, dated May 3, 2016, 11 pages.

"A Portable, Scalable Retinal Imaging System," TI Engibous Competition Report (Spring 2012), Rice University, http://www.ti.com/corp/docs/university/docs/Rice_University_mobileVision%20Final%20Report.pdf (96 pages).

Brown et al., "Comparison of image-assisted versus traditional fundus examination," Eye and Brain, Dovepress, Feb. 2013, vol. 5, pp. 1-8.

Dilating Eye Drops, AAPOS, http://web.archive.org/web/2012020409024/http://www.aapos.org/terms/conditions/43, Dilating Eye Drops, 2pgs, Dec. 17, 2015.

Girdwain, "Goggles Differentiate Between Stroke and Vertigo," Today's Geriatric Medicine, vol. 6 No. 4 p. 8, 2 pages (Oct. 1, 2013).

International Search Report and Written Opinion for Application No. PCT/US2016/015653 dated May 3, 2016, 11 pages.

Johns Hopkins Medicine, "Small Johns Hopkins-led study finds portable device diagnoses stroke with 100 percent accuracy," www.hopkinsmedicine.org/se/util/display_mod.cfm?module=/se-server/mod/modules/semod_printpage/mod_default_cfm&PageURL-/news/media/releases/is_i . . . , 2 pages (Mar. 5, 2013).

Muller et al., "Non-Mydriatic Confocal Retinal Imaging Using a Digital Light Projector," Ophthalmic Technologies XXIII, 2013, downloaded from: http://proceedings.spiedigitallibrary.org (8 pages).

Paques et al., "Panretinal, High-Resolution Color Photography of the Mouse Fundus," Investigative Ophthalmology & Visual Science, Jun. 2007, vol. 48, No. 6, pp. 2769-2774.

Spector, The Pupils, Clinical Methods: The History, Physical, and Laboratory Examinations, 3rd Edition, pp. 300-304, Chapter 58 (1990).

Visucampro NM—The Non-Mydriatic Fundus Camera System from Carl Zeiss, Carl Zeiss Meditec, International, 2005 (1 page).

Anastasakis et al., SLO—Infrared Imaging of the Macula and its Correlation with Functional Loss and Structural Changes in Patients with Stargardt Disease, May 1, 2012, 19pgs.

Carrasco-Zevallos, O. et al., "Pupil Tracking Optical Coherence Tomography for Precise Control of Pupil Entry Position," Biomedical Optics Express: 6(9): 3405-3419, Sep. 1, 2015, 15pgs.

Eidon—The First True Color Confocal Scanner on the Market, www.centervue.com, Jul. 27, 2015, 12pgs.

(56) References Cited

OTHER PUBLICATIONS

Grieve et al., Multi-wavelength imaging with the adaptive optics scnaning laser Ophthalmoscope, Optics Express 12230, Dec. 11, 2006, vol. 14, No. 25, 13pgs.
Hammer et al., Adaptive Optics Scanning Laser Ophthalmoscope for Stablized Retinal Imaging, Optics Express: 14(8): 3354-3367, Apr. 17, 2006, 14pgs.
Markow et al., "Real-Time Algorithm for Retinal Tracking," IEEE Transactions on Biomedical Engineering; 40(12): 1269-1281, Dec. 1993, 13pgs.
Moscaritolo et al., "A Machine Vision Method for Automated Alignment of Fundus Imaging Systems," Ophthalmic Surgery Lasers & Imaging: 41(6): 607-613, Sep. 29, 2010, 7pgs.
Navilas, Navigated Laser Therapy—A New Era in Retinal Disease Management, www.od-os.com, © 2015, 16pgs.
Sahin et al., "Adaptive Optics with Pupil Tracking for High Resolution Retinal Imaging," Biomedical Optics Express: 3(2): 225-239, Feb. 1, 2012, 15pgs.
Sheehy et al., "High-speed, Image-based eye tracking with a scanning laser ophthalmoscope," Biomedical Optics Express; 3(10): 2611-2622, Oct. 1, 2012, 12pgs.
Extended European Search Report for Application No. 16756033.3 dated Oct. 19, 2018.
International Search Report and Written Opinion for Application No. PCT/US2018/042223 dated Nov. 13, 2018, 16 pages.
Land, Edwin H., "The Retinex Theory of Color Visison," Scientific America, Dec. 1977, vol. 237 No. 6 p. 108-128.
User Manual Non-Mydriatic Retinal Camera, Topcon Corporation, Tokyo, Japan, 106 pages (2014).
Labeeb et al., "A Framework for Automatic Analysis of Digital Fundus Images," IEEE, pp. 5-10 (2013).
Extended European Search Report for Application No. 18834961.7 dated Feb. 23, 2021.

\* cited by examiner

THROUGH FOCUS RETINAL IMAGE CAPTURING

INTRODUCTION

People with type 1 or type 2 diabetes can develop eye disease as a result of having diabetes. One of the most common diabetic eye diseases is diabetic retinopathy, which is damage to the blood vessels of the light-sensitive tissue at the back of the eye, known as the retina. Trained medical professionals use cameras during eye examinations for diabetic retinopathy screening. The cameras can produce images of the back of the eye and trained medical professionals use those images to diagnose and treat diabetic retinopathy.

These images are produced either with pharmacological pupil dilation, known as mydriatic fundus imaging, or without pharmacological pupil dilation, known as non-mydriatic fundus imaging. Because pupil dilation is inversely related, in part, to the amount of ambient light, non-mydriatic fundus imaging usually occurs in low lighting environments. Medical professionals can also use fundus imaging apparatus to detect or monitor other diseases, such as hypertension, glaucoma, and papilledema.

SUMMARY

In one aspect, an apparatus for producing a non-mydriatic fundus image is disclosed. The apparatus can include a processor and memory, a light source, and a camera including a variable focus lens. The memory can store instructions that, when executed by the processor, cause the apparatus to adjust the focus of the lens to a plurality of different diopter ranges and capture a plurality of images of the fundus, where the camera captures at least one image at each of the different diopter ranges.

In another aspect, a method for capturing a non-mydriatic image of a fundus is disclosed. The method can include dividing a depth of field into a plurality of zones, adjusting a lens of a camera to focus on each of the plurality of zones and capturing at least one image at each of the plurality of zones.

In another aspect, a non-mydriatic image capture system is disclosed. The system can include a housing, an image capture device coupled to the housing and configured to capture images of an eye fundus of a subject, and a control module programmed to: instruct the image capture device to capture a plurality of images in a first image capture mode, process at least a portion of the plurality of images to determine a position of a pupil of the subject, and instruct the image capture device to capture an image in a second image capture mode when the position of the pupil is substantially aligned with an optical axis of the image capture device. The second image capture mode includes an illumination of a light source and a plurality of adjustments of a lens of the image capture device such that the image capture device captures an image at each of the plurality of adjustments in a depth of field focus range.

DESCRIPTION OF THE FIGURES

The following figures, which form a part of this application, are illustrative of described technology and are not meant to limit the scope of the claims in any manner, which scope shall be based on the claims appended hereto.

DETAILED DESCRIPTION

Figure 1:
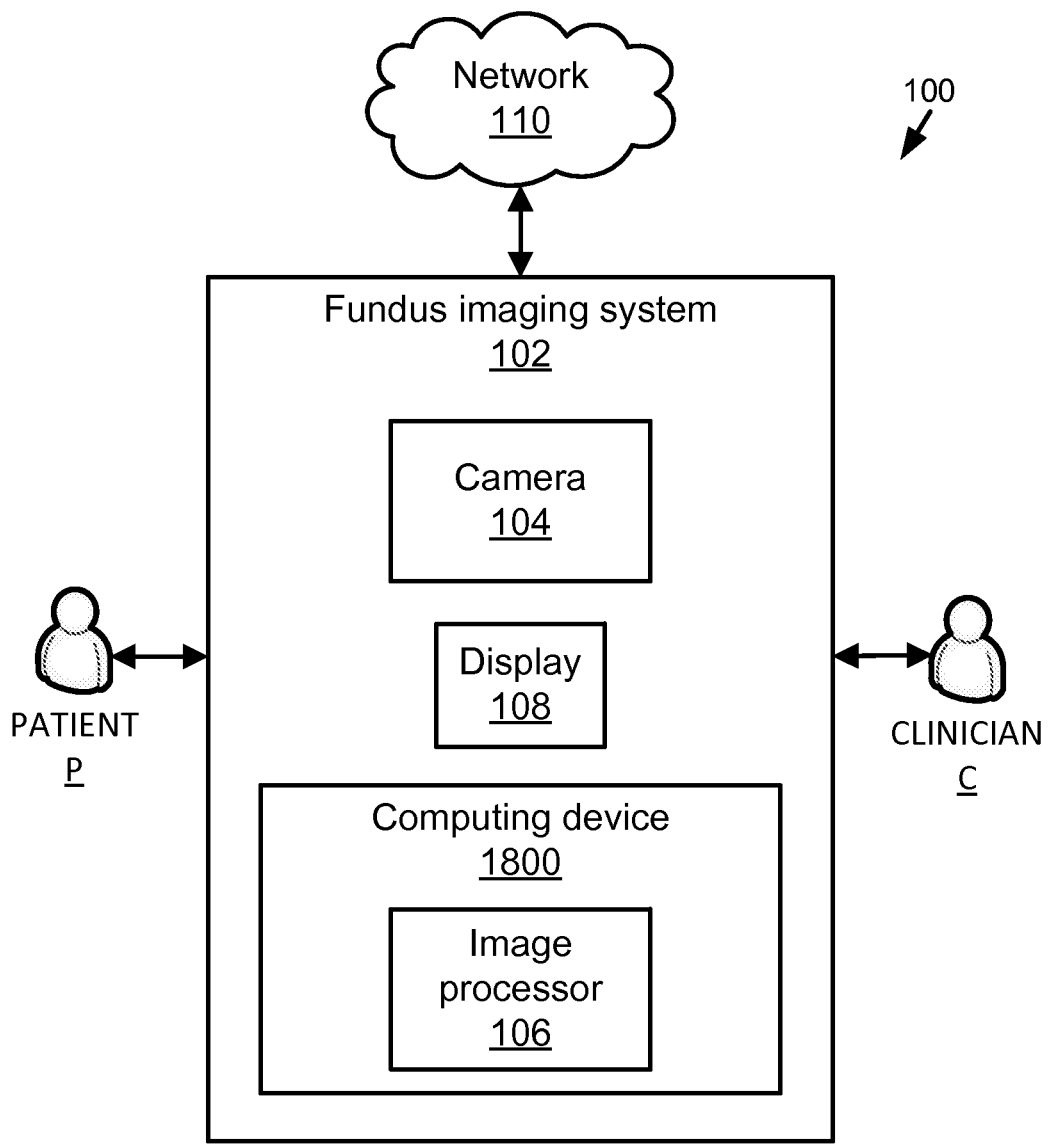
FIG. 1 is an embodiment of an example system for recording and viewing an image of a patient's fundus.

FIG. 1 is a schematic block diagram illustrating an example system 100 for recording and viewing an image of a patient's fundus. In this example, the system 100 includes a patient P, a fundus imaging system 102, a computing device 1800 including an image processor 106, a camera 104 in communication with the computing device 1800, a display 108 in communication with the computing device 1800 and used by clinician C, and a network 110. An embodiment of the example fundus imaging system 102 is shown and described in more detail below with reference to FIG. 4.

The fundus imaging system 102 functions to create a set of digital image of a patient's P eye fundus. As used herein, "fundus" refers to the eye fundus and includes the retina, optic nerve, macula, vitreous, choroid and posterior pole.

In this example, one or more images of the eye are desired. For instance, the patient P is being screened for an eye disease, such as diabetic retinopathy. The fundus imaging system 102 can also be used to provide images of the eye for other purposes, such as to diagnose or monitor the progression of a disease such as diabetic retinopathy.

The fundus imaging system 102 includes a handheld housing that supports the system's components. The housing supports one or two apertures for imaging one or two eyes at a time. In embodiments, the housing supports positional guides for the patient P, such as an optional adjustable chin rest. The positional guide or guides help to align the patient's P eye or eyes with the one or two apertures. In embodiments, the housing supports means for raising and lowering the one or more apertures to align them with the patient's P eye or eyes. Once the patient's P eyes are aligned, the clinician C then initiates the image captures by the fundus imaging system 102.

One technique for fundus imaging requires mydriasis, or the dilation of the patient's pupil, which can be painful and/or inconvenient to the patient P. Example system 100 does not require a mydriatic drug to be administered to the patient P before imaging, although the system 100 can image the fundus if a mydriatic drug has been administered.

The system 100 can be used to assist the clinician C in screening for, monitoring, or diagnosing various eye diseases, such as hypertension, diabetic retinopathy, glaucoma and papilledema. It will be appreciated that the clinician C that operates the fundus imaging system 102 can be different from the clinician C evaluating the resulting image.

In the example embodiment 100, the fundus imaging system 102 includes a camera 104 in communication with an image processor 106. In this embodiment, the camera 104 is a digital camera including a lens, an aperture, and a sensor array. The camera 104 lens is a variable focus lens, such as a lens moved by a step motor, or a fluid lens, also known as a liquid lens in the art. The camera 104 is configured to record images of the fundus one eye at a time. In other embodiments, the camera 104 is configured to record an image of both eyes substantially simultaneously. In those embodiments, the fundus imaging system 102 can include two separate cameras, one for each eye.

In example system 100, the image processor 106 is operatively coupled to the camera 104 and configured to communicate with the network 110 and display 108.

The image processor 106 regulates the operation of the camera 104. Components of an example computing device, including an image processor, are shown in more detail in FIG. 7, which is described further below.

The display 108 is in communication with the image processor 106. In the example embodiment, the housing supports the display 108. In other embodiments, the display connects to the image processor, such as a smart phone, tablet computer, or external monitor. The display 108 functions to reproduce the images produced by the fundus imaging system 102 in a size and format readable by the clinician C. For example, the display 108 can be a liquid crystal display (LCD) and active matrix organic light emitting diode (AMOLED) display. The display can be touch sensitive.

The example fundus imaging system 102 is connected to a network 110. The network 110 may include any type of wireless network, a wired network, or any communication network known in the art. For example, wireless connections can include cellular network connections and connections made using protocols such as 802.11a, b, and/or g. In other examples, a wireless connection can be accomplished directly between the fundus imaging system 102 and an external display using one or more wired or wireless protocols, such as Bluetooth, Wi-Fi Direct, radio-frequency identification (RFID), or Zigbee. Other configurations are possible.

Figure 2:
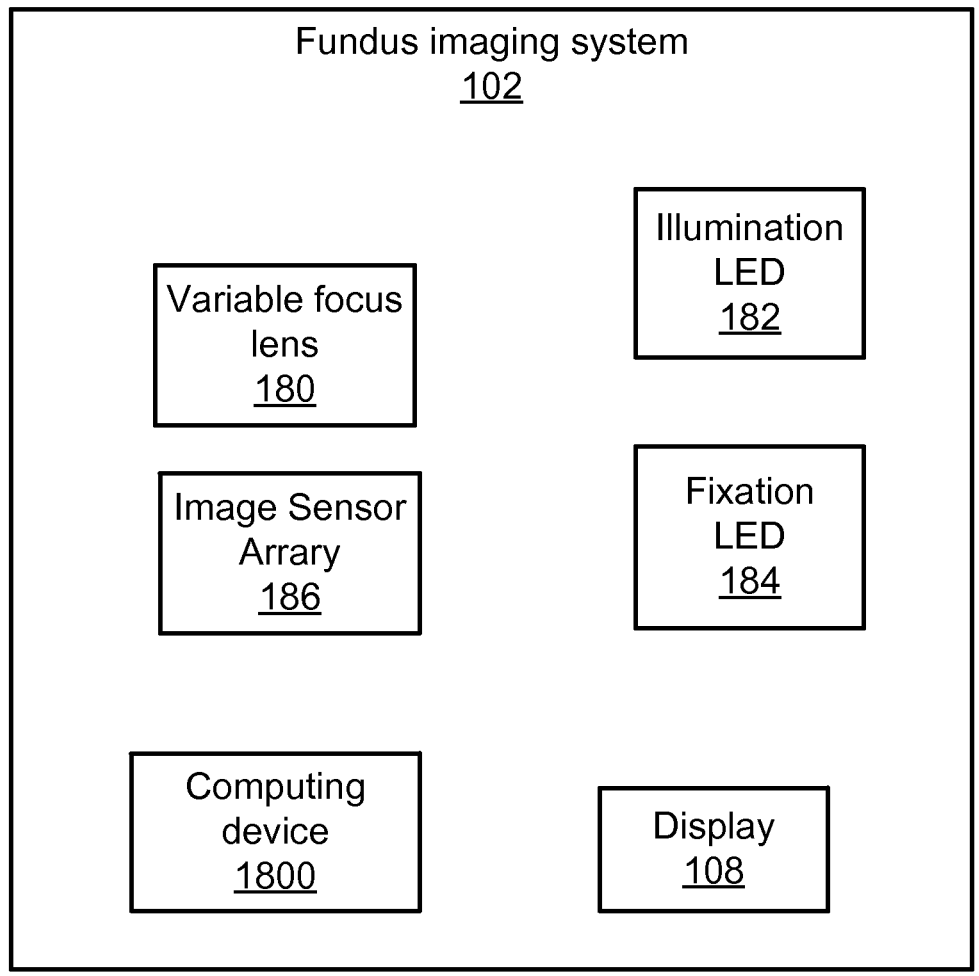
FIG. 2 is an embodiment of an example fundus imaging system.

FIG. 2 illustrates components of an example fundus imaging system 102. The example fundus imaging system 102 includes a variable focus lens 180, an illumination LED 182, an image sensor array 186, a fixation LED 184, a computing device 1800, and a display 108. Each component is in electrical communication with, at least, the computing device 1800. Other embodiments can include more or fewer components.

In one of the embodiments, the variable focus lens 180 is a liquid lens. A liquid lens is an optical lens whose focal length can be controlled by the application of an external force, such as a voltage. The lens includes a transparent fluid, such as water or water and oil, sealed within a cell and a transparent membrane. By applying a force to the fluid, the curvature of the fluid changes, thereby changing the focal length. This effect is known as electrowetting.

Generally, a liquid lens can focus between about −10 diopters to about +30 diopters. The focus of a liquid lens can be made quickly, even with large changes in focus. For instance, some liquid lenses can autofocus in tens of milliseconds or faster. Liquid lenses can focus from about 10 cm to infinity and can have an effective focal length of about 16 mm or shorter.

In another embodiment of example fundus imaging system 102, the variable focus lens 180 is one or more movable lenses that are controlled by a stepping motor, a voice coil, an ultrasonic motor, or a piezoelectric actuator. Additionally, a stepping motor can also move the image sensor array 186. In those embodiments, the variable focus lens 180 and/or the image sensor array 186 are oriented normal to an optical axis of the fundus imaging system 102 and move along the optical axis. An example stepping motor is shown and described below with reference to FIG. 4.

The example fundus imaging system 102 also includes an illumination light-emitting diode (LED) 182. The illumination LED 182 can be single color or multi-color. For example, the illumination LED 182 can be a three-channel RGB LED, where each die is capable of independent and tandem operation.

Optionally, the illumination LED 182 is an assembly including one or more visible light LEDs and a near-infrared LED. The optional near-infrared LED can be used in a preview mode, for example, for the clinician C to determine or estimate the patient's P eye focus without illuminating visible light that could cause the pupil to contract or irritate the patient P.

The illumination LED 182 is in electrical communication with the computing device 1800. Thus, the illumination of illumination LED 182 is coordinated with the adjustment of the variable focus lens 180 and image capture. The illumination LED 182 can be overdriven to draw more than the maximum standard current draw rating. In other embodiments, the illumination LED 182 can also include a near-infrared LED. The near-infrared LED is illuminated during a preview mode.

The example fundus imaging system 102 also optionally includes a fixation LED 184. The fixation LED 184 is in communication with the computing device 1800 and produces a light to guide the patient's P eye for alignment. The fixation LED 184 can be a single color or multicolor LED. For example, the fixation LED 184 can produce a beam of green light that appears as a green dot when the patient P looks into the fundus imaging system 102. Other colors and designs, such as a cross, "x" and circle are possible.

The example fundus imaging system 102 also includes an image sensor array 186 that receives and processes light reflected by the patient's fundus. The image sensor array 186 is, for example, a complementary metal-oxide semiconductor (CMOS) sensor array, also known as an active pixel sensor (APS), or a charge coupled device (CCD) sensor.

The image sensor array 186 has a plurality of rows of pixels and a plurality of columns of pixels. In some embodiments, the image sensor array has about 1280 by 1024 pixels, about 640 by 480 pixels, about 1500 by 1152 pixels, about 2048 by 1536 pixels, or about 2560 by 1920 pixels.

In some embodiments, the pixel size in the image sensor array 186 is from about four micrometers by about four micrometers; from about two micrometers by about two micrometers; from about six micrometers by about six micrometers; or from about one micrometer by about one micrometer.

The example image sensor array 186 includes photodiodes that have a light-receiving surface and have substantially uniform length and width. During exposure, the photodiodes convert the incident light to a charge. The image sensor array 186 can be operated as a global reset, that is, substantially all of the photodiodes are exposed simultaneously and for substantially identical lengths of time.

The example fundus imaging system 102 also includes a display 108, discussed in more detail above with reference to FIG. 1. Additionally, the example fundus imaging system 102 includes a computing device 1800, discussed in more detail below with reference to FIG. 7.

Figure 3:
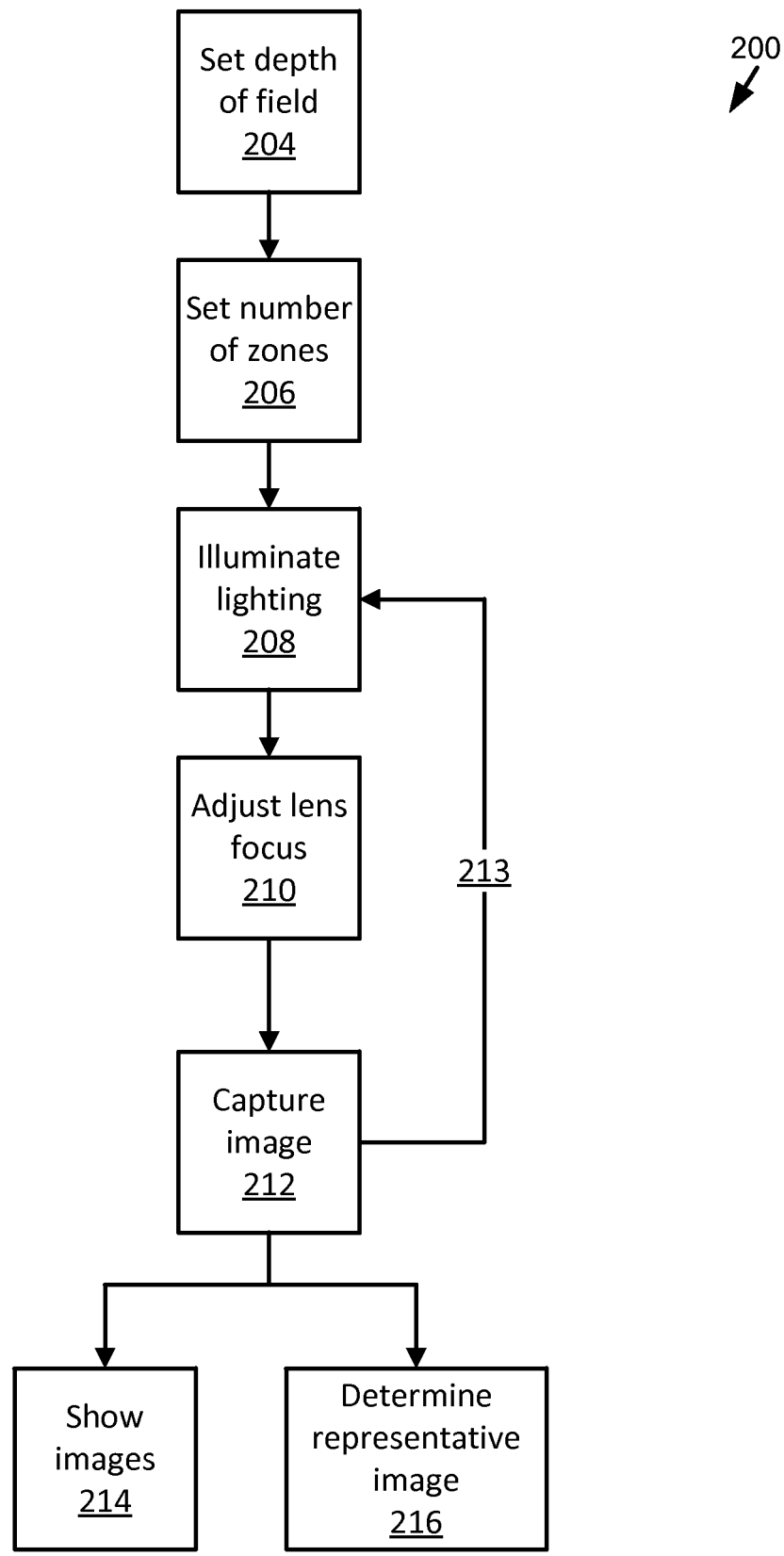
FIG. 3 is an embodiment of an example method for imaging a patient's fundus using a fundus imaging system.

FIG. 3 is an embodiment of a method 200 for imaging a patient's fundus using a fundus imaging system. In the embodiment shown, the lighting is optimally dimmed prior to execution, although lowering the lighting is optional. The embodiment shown includes a set depth of field operation 204, a set number of zones operation 206, an illuminate lighting operation 208, an adjust lens focus operation 210, a capture image operation 212, repeat operation(s) 213, a show images operation 214 and a determine representative image operation 216. Other embodiments can include more or fewer steps.

The embodiment of method 200 begins with setting a depth of field operation 204. In embodiments, the variable focus lens 180 is capable of focusing from about −20 diopters to about +20 diopters. Set depth of field operation 204 defines the lower and upper bounds in terms of diopters. For example, the depth of field range could be set to about −10 to +10 diopters; about −5 to about +5 diopters; about −10 to about +20 diopters; about −5 to about +20 diopters; about −20 to about +0 diopters; or about −5 to about +5 diopters. Other settings are possible. The depth of field can be preprogrammed by the manufacturer. Alternatively, the end user, such as the clinician C, can set the depth of field.

As shown in FIG. 3, the next operation in embodiment of method 200 is setting the number of zones operation 206. However, zones operation 206 can occur before or concurrent with field operation 204. In zones operation 206, the depth of field is divided into equal parts, where each part is called a zone. In other embodiments, the zones are not all equal. The number of zones is equal to the number of images captured in capture image operation 212.

For example, when the depth of field is from −10 to +10 diopters, the focus of the variable focus lens can be changed by 4 diopters before each image capture. Thus, in this example, images would be captured at −10, −6, −2, +2, +6 and +10 diopters. Or, images could be captured at −8, −4, 0, +4 and +8 diopters, thereby capturing an image in zones −10 to −6 diopters, −6 to −2 diopters, −2 to +2 diopters, +2 to +6 diopters and +6 to +10 diopters, respectively. In that instance, the depth of focus is about +/−2 diopters. Of course, the number of zones and the depth of field can vary, resulting in different ranges of depth of field image capture.

In embodiments, both depth of field and number of zones are predetermined. For example, −10 D to +10 D and 5 zones. Both can be changed by a user.

After the depth of field and number of zones are set, the next operation in embodiment of method 200 is the image capture process, which includes illuminate lighting operation 208, adjust lens focus operation 210 and capture image operation 212. As shown in FIG. 3, the lighting component is illuminated (lighting operation 208) before the lens focus is adjusted (lens focus operation 210). However, lens focus operation 210 can occur before or concurrent with lighting operation 208.

The illumination LED 182 is illuminated in lighting operation 208. The illumination LED 182 can remain illuminated throughout the duration of each image capture. Alternatively, the illumination LED 182 can be turned on and off for each image capture. In embodiments, the illumination LED 182 only turns on for the same period of time as the image sensor array 186 exposure time period.

Optionally, lighting operation 208 can additionally include illuminating a near-infrared LED. The clinician C can use the illumination of the near-infrared LED as a way to preview the position of the patient's P pupil.

The focus of variable focus lens 180 is adjusted in lens focus operation 210. Autofocusing is not used in embodiment of method 200. That is, the diopter setting is provided to the lens without regard to the quality of the focus of the image. Indeed, traditional autofocusing fails in the low-lighting non-mydriatic image capturing environment. The embodiment of method 200 results in a plurality of images at least one of which, or a combination of which, yields an in-focus view of the patient's P fundus.

Additionally, the lack of autofocusing enables the fundus imaging system 102 to rapidly capture multiple images in capture image operation 212 at different diopter ranges. That is, variable focus lens 180 can be set to a particular diopter range and an image captured without the system verifying that the particular focus level will produce an in-focus image, as is found in autofocusing systems. Because the system does not attempt to autofocus, and the focus of the variable focus lens 180 can be altered in roughly tens of milliseconds, images can be captured throughout the depth of field in well under a second, in embodiments. Thus, in the embodiment of method 200, the fundus imaging system 102 can capture images of the entire depth of field before the patient's P eye can react to the illuminated light. Without being bound to a particular theory, depending on the patient P, the eye might react to the light from illumination LED 182 in about 150 milliseconds.

The image sensor array 186 captures an image of the fundus in capture image operation 212. As discussed above, the embodiment of method 200 includes multiple image captures of the same fundus at different diopter foci. The example fundus imaging system 102 uses a global reset or global shutter array, although other types of shutter arrays, such as a rolling shutter, can be used. The entire image capture method 200 can also be triggered by passive eye tracking and automatically capture, for example, 5 frames of images. An embodiment of example method for passive eye tracking is shown and described in more detail with reference to FIG. 5, below.

After the fundus imaging system 102 captures an image of the fundus, the embodiment of method 200 returns in loop 213 to either the illuminate lighting operation 208 or the adjust lens focus operation 210. That is, operations 208, 210 and 212 are repeated until an image is captured in each of the preset zones from zones operation 206. It is noted that the image capture does not need to be sequential through the depth of field. Additionally, each of the images does not need to be captured in a single loop; a patient could have one or more fundus images captured and then one or more after a pause or break.

After an image is captured in each of the zones (capture image operation 212) in embodiment of method 200, either the images are displayed in show images operation 214 or a representative image is determined in operation 216 and then the image is displayed. Show images operation 214 can include showing all images simultaneously or sequentially on display 108. A user interface shown on display 108 can then enable the clinician C or other reviewing medical professional to select or identify the best or a representative image of the patient's P fundus.

In addition to, or in place of, show images operation 214, the computing device can determine a representative fundus image in operation 216. Operation 216 can also produce a single image by compiling aspects of one or more of the images captured. This can be accomplished by, for example, using a wavelet feature reconstruction method to select, interpolate, and/or synthesize the most representative frequency or location components.

The fundus imaging system 102 can also produce a three-dimensional image of the fundus by compiling the multiple captured images. Because the images are taken at different focus ranges of the fundus, the compilation of the pictures can contain three-dimensional information about the fundus.

In turn, the image or images from operation 214 or 216 can be sent to a patient's electronic medical record or to a different medical professional via network 110.

Figure 4:
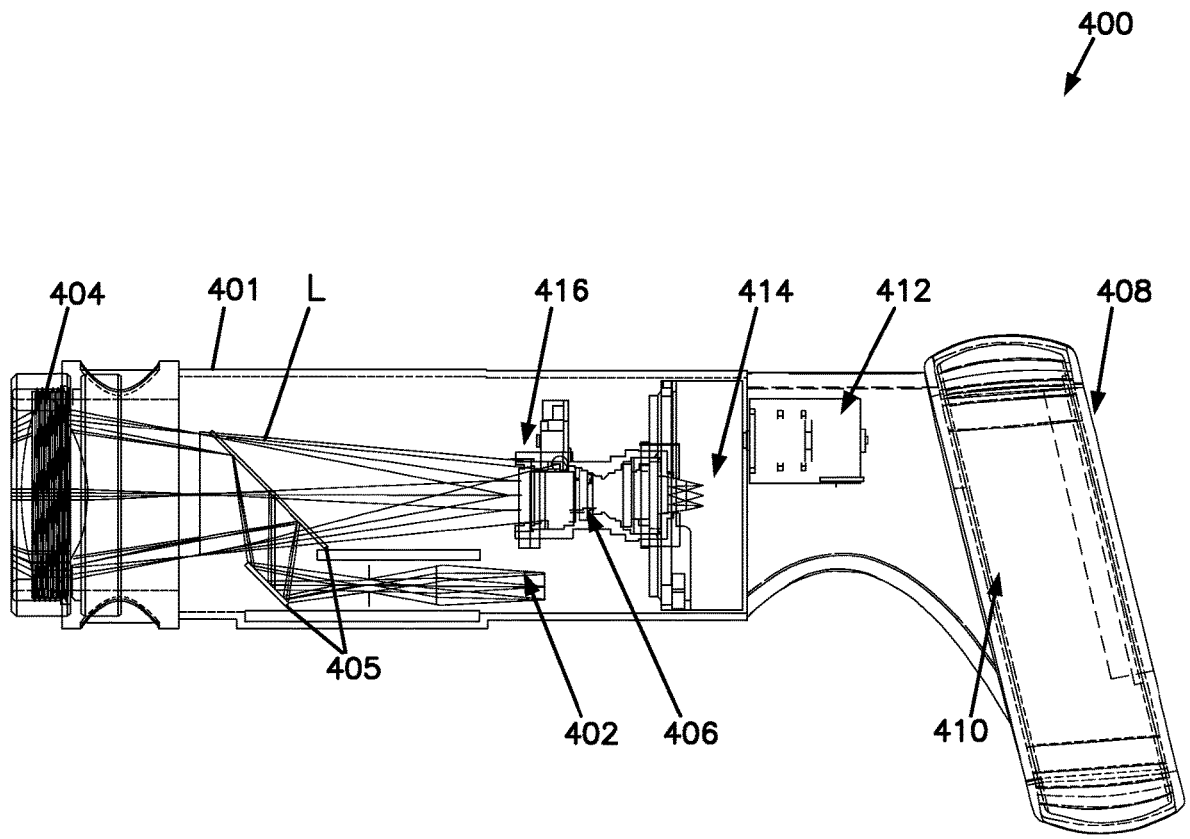
FIG. 4 is an embodiment of an example fundus imaging system.

FIG. 4 illustrates an embodiment of example fundus imaging system 400. The embodiment 400 includes a housing 401 that supports an optional fixation LED 402, an objective lens 404, fixation LED mirrors 405, variable focus lens assembly 406, display 408, printed circuit board 410, step motor 412, image sensor array 414, and illumination LED 416. Also shown in FIG. 4 are light paths L that include potential light paths from optional fixation LED 402 and incoming light paths from outside the fundus imaging system 400. The illustrated components have the same or similar functionality to the corresponding components discussed above with reference to FIGS. 1-3 above. Other embodiments can include more or fewer components.

The housing 401 of example fundus imaging system 400 is sized to be hand held. In embodiments, the housing 401 additionally supports one or more user input buttons near display 408, not shown in FIG. 4. The user input button can initiate the image capture sequence, at least a portion of which is shown and discussed with reference to FIG. 3, above. Thus, the fundus imaging system 400 is capable of being configured such that the clinician C does not need to adjust the lens focus.

Fixation LED 402 is an optional component of the fundus imaging system 400. The fixation LED 402 is a single or multi-colored LED. Fixation LED 402 can be more than one LED.

As shown in FIG. 4, pivoting mirrors 405 can be used to direct light from the fixation LED 402 towards the patient's pupil. Additionally, an overlay or filter can be used to project a particular shape or image, such as an "X", to direct the patient's focus. The pivoting mirrors 405 can control where the fixation image appears in the patient's view. The pivoting mirrors 405 do not affect the light reflected from the patient's fundus.

The embodiment of example fundus imaging system 400 also includes a variable focus lens assembly 406. As shown in FIG. 4, the variable focus lens assembly 406 is substantially aligned with the longitudinal axis of the housing 401. Additionally, the variable focus lens assembly 406 is positioned between the objective lens 404 and the image sensor array 414 such that it can control the focus of the incident light L onto the image sensor array.

The example printed circuit board 410 is shown positioned within one distal end of the housing 401 near the display 408. However, the printed circuit board 410 can be positioned in a different location. The printed circuit board 410 supports the components of the example computing device 1800. A power supply can also be positioned near printed circuit board 410 and configured to power the components of the embodiment of example fundus imaging system 400.

Step motor 412 is an optional component in the example embodiment 400. Step motor 412 can also be, for example, a voice coil, an ultrasonic motor, or a piezoelectric actuator. In the example embodiment 400, step motor 412 moves the variable focus lens assembly 406 and/or the sensor array 414 to achieve variable focus. The step motor 412 moves the variable focus lens assembly 406 or the sensor array 414 in a direction parallel to a longitudinal axis of the housing 401 (the optical axis). The movement of step motor 412 is actuated by computing device 1800.

The example image sensor array 414 is positioned normal to the longitudinal axis of the housing 401. As discussed above, the image sensor array 414 is in electrical communication with the computing device. Also, as discussed above, the image sensor array can be a CMOS (APS) or CCD sensor.

An illumination LED 416 is positioned near the variable focus lens assembly 406. However, the illumination LED 416 can be positioned in other locations, such as near or with the fixation LED 402.

Figure 5:
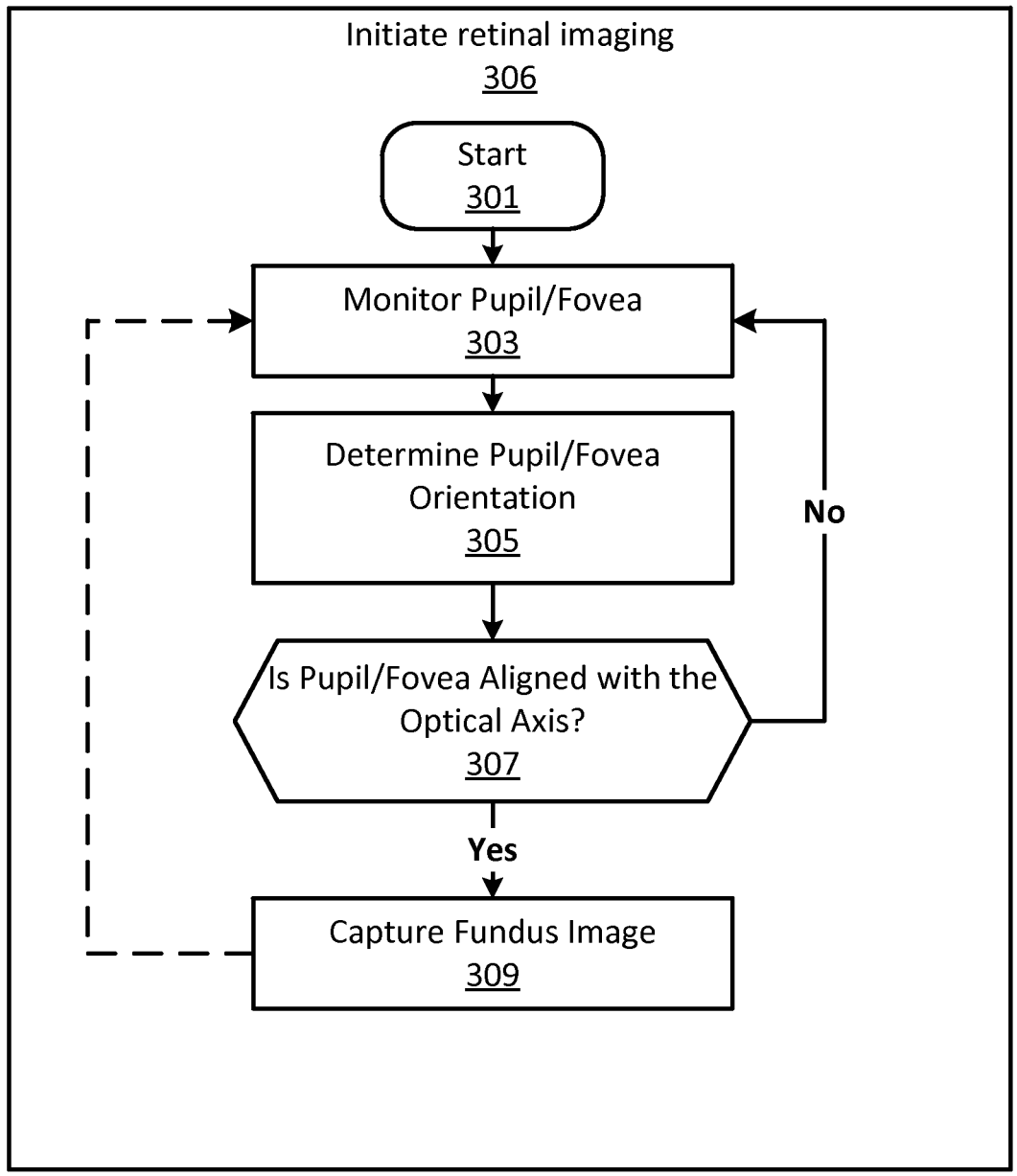
FIG. 5 illustrates an example method of initiating a fundus imaging using passive eye tracking.

FIG. 5 illustrates an alternate embodiment of initiate retinal imaging step 306 using passive eye tracking. The initiate retinal imaging step 306 operates to image the fundus of the patient P using passive eye tracking. In the initiate retinal imaging step 306, the fundus imaging system 102 monitors the pupil/fovea orientation of the patient P. Although the initiate retinal imaging step 306 is described with respect to fundus imaging system 102, the initiate retinal imaging step 306 may be performed using a wearable or nonwearable fundus imaging system, such as a handheld digital fundus imaging system.

Initially, at step 303, the pupil or fovea or both of the patient P are monitored. The fundus imaging system 102 captures images in a first image capture mode. In the first image capture mode, the fundus imaging system 102 captures images at a higher frame rate. In some embodiments, in the first image capture mode, the fundus imaging system 102 captures images with infra-red illumination and at lower resolutions. In some embodiments, the infra-red illumination is created by the illumination LED 182 operating to generate and direct light of a lower intensity towards the subject. The first image capture mode may minimize discomfort to the patient P, allow the patient P to relax, and allow for a larger pupil size without dilation (non-mydriatic).

Next, at step 305, the computing system 1800 processes at least a portion of the images captured by the fundus imaging system 102. The computing system 1800 processes the images to identify the location of the pupil or fovea or both of the patient P. Using the location of the pupil or fovea or both in one of the images, a vector corresponding to the pupil/fovea orientation is calculated. In some embodiments, the pupil/fovea orientation is approximated based on the distance between the pupil and fovea in the image. In other embodiments, the pupil/fovea orientation is calculated by approximating the position of the fovea relative to the pupil in three dimensions using estimates of the distance to the pupil and the distance between the pupil and the fovea. In other embodiments, the pupil/fovea orientation is approximated from the position of the pupil alone. In yet other embodiments, other methods of approximating the pupil/fovea orientation are used.

Next, at step 307, the pupil/fovea orientation is compared to the optical axis of the fundus imaging system 102. If the pupil/fovea orientation is substantially aligned with the optical axis of the fundus imaging system 102, the process proceeds to step 309 to capture a fundus image. If not, the process returns to step 303 to continue to monitor the pupil or fovea. In some embodiments, the pupil/fovea orientation is substantially aligned with the optical axis when the angle between them is less than two to fifteen degrees.

Next, at step 309, fundus images are captured by triggering the embodiment of example thru focusing image capturing method 200. In embodiments, five images are captured at step 309. In some embodiments, the fundus image is captured in a second image capture mode. In some embodiments, in the second image capture mode, the fundus imaging system 102 captures images with visible illumination and at higher resolutions. In some embodiments, the visible illumination is created by the illumination LED 182 operating to generate and direct light of a higher intensity towards the subject. In other embodiments, the higher illumination is created by an external light source or ambient light. The second image capture mode may facilitate capturing a clear, well-illuminated, and detailed fundus image.

Figure 6:
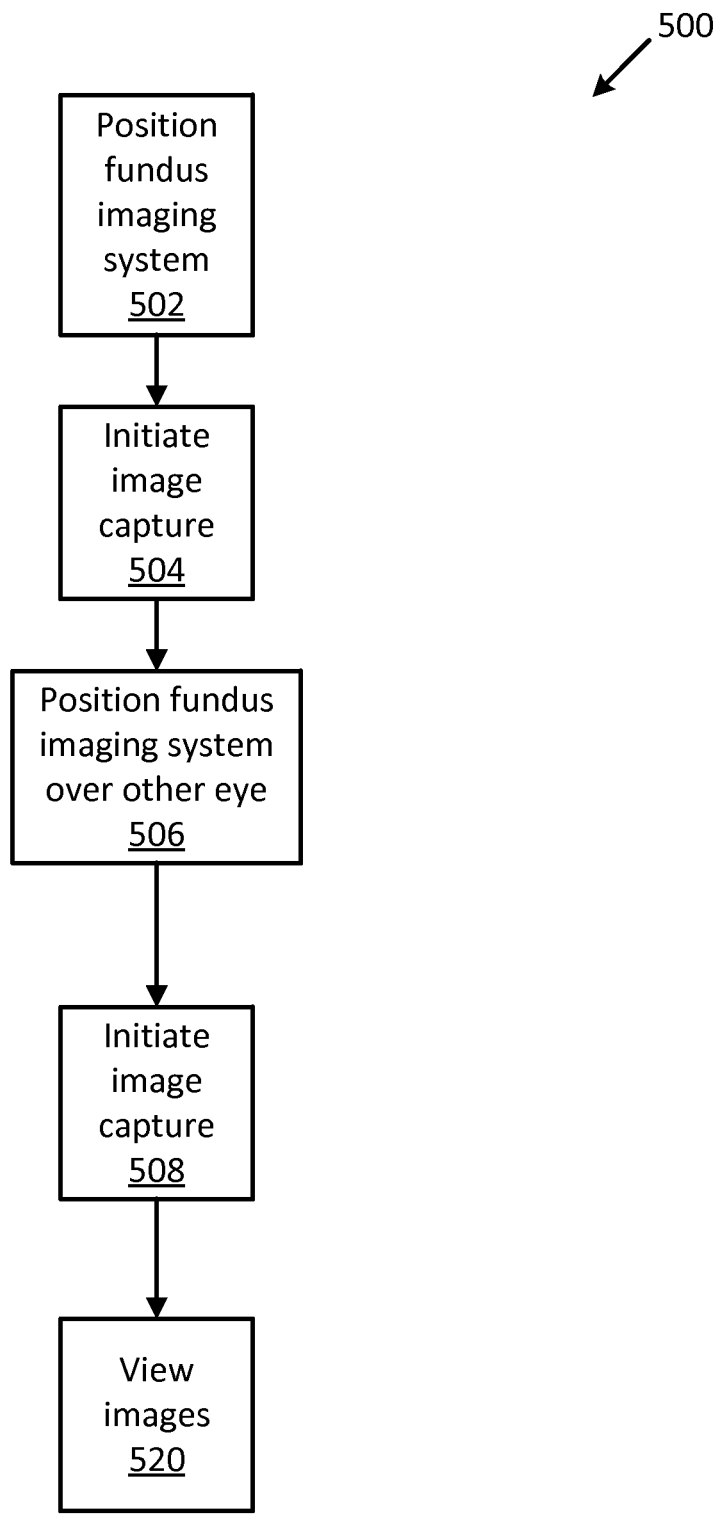
FIG. 6 is an embodiment of an example use of a fundus imaging system.

In some embodiments, after step 309, the initiate retinal imaging step 306 returns to step 303 to continue to monitor the pupil/fovea orientation. The initiate retinal imaging step 306 may continue to collect fundus images indefinitely or until a specified number of images have been collected. Further information regarding passive eye tracking can be found in U.S. patent application Ser. No. 14/177,594, titled Ophthalmoscope Device, which is hereby incorporated by reference in its entirety FIG. 6 is an embodiment of example use 500 of fundus imaging system 102. In the embodiment of example use 500, a clinician positions the fundus imaging system (operation 502), initiates image capture (operation 504), positions the fundus imaging system over the other eye (operation 506), initiates image capture (operation 508), and views images (operation 520). Although the example use 500 is conducted without first administering mydriatic pharmaceuticals, the example use 500 can also be performed for a patient who has taken a pupil-dilating compound. The embodiment of example use 500 can also include lowering the lighting. The embodiment of example use 500 is conducted using the same or similar components as those described above with reference to FIGS. 1-3. Other embodiments can include more or fewer operations.

The embodiment of example use 500 begins by positioning the fundus imaging system (operation 502). In embodiments, the clinician first initiates an image capture sequence via a button on the housing or a graphical user interface shown by the display. The graphical user interface can instruct the clinician to position the fundus imaging system over a particular eye of the patient. Alternatively, the clinician can use the graphical user interface to indicate which eye fundus is being imaged first.

In operation 502, the clinician positions the fundus imaging system near the patient's eye socket. The clinician positions the aperture of the system flush against the patient's eye socket such that the aperture, or a soft material eye cup extending from the aperture, seals out most of the ambient light. Of course, the example use 500 does not require positioning the aperture flush against the patient's eye socket.

When the fundus imaging system is in position, the system captures more than one image of the fundus in operation 504. As discussed above, the system does not require the clinician to manually focus the lens. Additionally, the system does not attempt to autofocus on the fundus. Rather, the clinician simply initiates the image capture, via a button or the GUI, and the fundus imaging system controls when to capture the images and the focus of the variable focus lens. Also, as discussed above at least with reference to FIG. 5, the system can initiate image capture using passive eye tracking.

The patient may require the fundus imaging system to be moved away from the eye socket during image capture operation 504. The clinician can re-initiate the image capture sequence of the same eye using the button or the GUI on the display.

After capturing an image in each of the specified zones, the fundus imaging system notifies the clinician that the housing should be positioned over the other eye (operation 506). The notification can be audible, such as a beep, and/or the display can show a notification. In embodiments, the system is configured to capture a set of images of only one eye, wherein the example method 500 proceeds to view images operation 520 after image capture operation 504.

Similar to operation 502, the clinician then positions the fundus imaging system near or flush with the patient's other eye socket in operation 506. Again, when the system is in place, an image is captured in every zone in operation 508.

After images have been captured of the fundus in each pre-set zone, the clinician can view the resulting images in operation 520. As noted above with reference to FIG. 3, the images can be post-processed before the clinician views the images to select or synthesize a representative image. Additionally, the fundus images can be sent to a remote location for viewing by a different medical professional.

Figure 7:
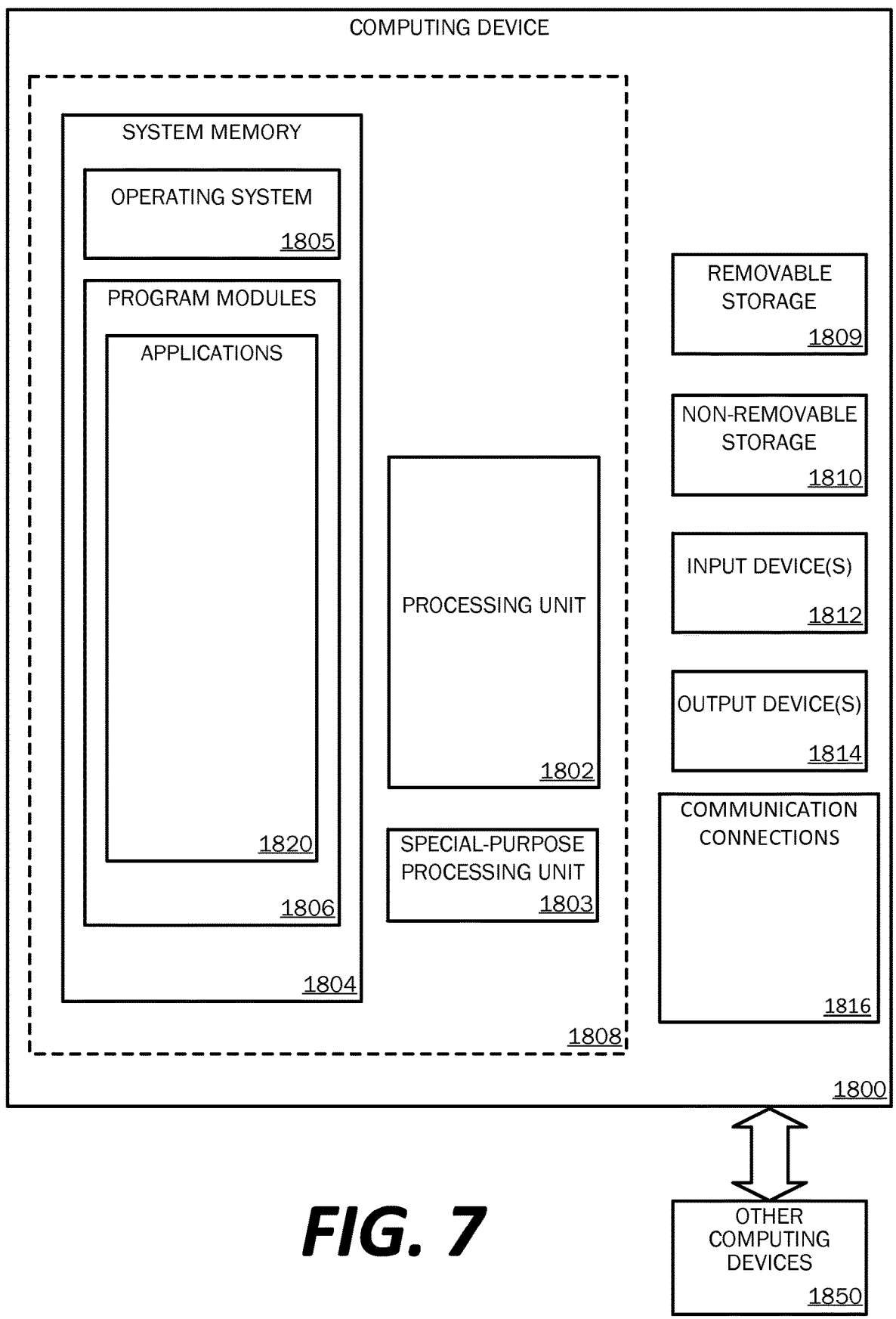
FIG. 7 is an example computing device used within the fundus imaging system.

FIG. 7 is a block diagram illustrating physical components (i.e., hardware) of a computing device 1800 with which embodiments of the disclosure may be practiced. The computing device components described below may be suitable to act as the computing devices described above, such as wireless computing device and/or medical device of FIG. 1. In a basic configuration, the computing device 1800 may include at least one processing unit 1802 and a system memory 1804. Depending on the configuration and type of computing device, the system memory 1804 may comprise, but is not limited to, volatile storage (e.g., random access memory), non-volatile storage (e.g., read-only memory), flash memory, or any combination of such memories. The system memory 1804 may include an operating system 1805 and one or more program modules 1806 suitable for running software applications 1820. The operating system 1805, for example, may be suitable for controlling the operation of the computing device 1800. Furthermore, embodiments of the disclosure may be practiced in conjunction with a graphics library, other operating systems, or any other application program and is not limited to any particular application or system. This basic configuration is illustrated in FIG. 7 by those components within a dashed line 1808. The computing device 1800 may have additional features or functionality. For example, the computing device 1800 may also include additional data storage devices (removable and/or non-removable) such as, for example, magnetic disks, optical disks, or tape. Such additional storage is illustrated in FIG. 7 by a removable storage device 1809 and a non-removable storage device 1810.

As stated above, a number of program modules and data files may be stored in the system memory 1804. While executing on the processing unit 1802, the program modules 1806 may perform processes including, but not limited to, generate list of devices, broadcast user-friendly name, broadcast transmitter power, determine proximity of wireless computing device, connect with wireless computing device, transfer vital sign data to a patient's EMR, sort list of wireless computing devices within range, and other processes described with reference to the figures as described herein. Other program modules that may be used in accordance with embodiments of the present disclosure, and in particular to generate screen content, may include electronic mail and contacts applications, word processing applications, spreadsheet applications, database applications, slide presentation applications, drawing or computer-aided application programs, etc.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 7 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, may be operated via application-specific logic integrated with other components of the computing device 1800 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

The computing device 1800 may also have one or more input device(s) 1812 such as a keyboard, a mouse, a pen, a sound or voice input device, a touch or swipe input device, etc. The output device(s) 1814 such as a display, speakers, a printer, etc. may also be included. The aforementioned devices are examples and others may be used. The computing device 1800 may include one or more communication connections 1816 allowing communications with other computing devices. Examples of suitable communication connections 1816 include, but are not limited to, RF transmitter, receiver, and/or transceiver circuitry; universal serial bus (USB), parallel, and/or serial ports.

The term computer readable media as used herein may include non-transitory computer storage media. Computer storage media may include volatile and nonvolatile, removable and non-removable media implemented in any method or technology for storage of information, such as computer readable instructions, data structures, or program modules. The system memory 1804, the removable storage device 1809, and the non-removable storage device 1810 are all computer storage media examples (i.e., memory storage.) Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 1800. Any such computer storage media may be part of the computing device 1800. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Although the example medical devices described herein are devices used to monitor patients, other types of medical devices can also be used. For example, the different components of the CONNEX™ system, such as the intermediary servers that communication with the monitoring devices, can also require maintenance in the form of firmware and software updates. These intermediary servers can be managed by the systems and methods described herein to update the maintenance requirements of the servers.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

While embodiments have been described, it will be understood that those skilled in the art, both now and in the future, may make various improvements and enhancements can be made.

As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussions regarding ranges and numerical data. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5; etc. This same principle applies to ranges reciting only one numerical value. Furthermore, such an interpretation should apply regardless of the breadth of the range or the characteristics being described.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. An apparatus for producing a non-mydriatic fundus image, comprising:

a processor and a memory;

an illumination component including a visible light source and operatively coupled to the processor;

a camera including a lens and operatively coupled to the processor; and a display coupled to the memory and to the processor, wherein the memory stores instructions that, when executed by the processor, cause the apparatus to:

set a depth of field for capturing a plurality of images of a fundus, the depth of field being set by defining lower and upper diopters;

divide the depth of field into a plurality of different diopter ranges, wherein the depth of field and number of diopter ranges are adjustable;

adjust the lens to each of the plurality of different diopter ranges, the lens being set to each diopter range without regard to focus of features shown by the lens;

capture, using the camera, a plurality of images of a fundus, wherein the camera captures at least one image within each of the plurality of different diopter ranges;

illuminate, using the illumination component, visible light during the capture of the plurality of images;

after capturing each of the plurality of images of the fundus:

evaluate each of the plurality of images of the fundus; and based on the evaluation of each of the plurality of images of the fundus, determine a representative image of the fundus from the plurality of images; and display the representative image of the fundus.

2. The apparatus of claim 1, wherein the instructions further cause the apparatus to: adjust the focus of the lens and capture the plurality of images until images have been captured in a depth of field from −10 diopters to +10 diopters.

3. The apparatus of claim 2, wherein each adjustment of the focus is by +/−1 diopter.

4. The apparatus of claim 2, wherein each adjustment of the focus is by +/−2 diopters.

5. The apparatus of claim 2, wherein the images are captured sequentially in less than about 150 milliseconds.

6. A method for capturing a non-mydriatic image of a fundus, comprising:

setting a depth of field for capturing a plurality of images of a fundus, the depth of field being set by defining lower and upper diopters;

dividing the depth of field into a plurality of zones, each zone comprising a diopter range within the depth of field, wherein the depth of field and number of zones are adjustable;

adjusting a lens of a camera on each of the plurality of zones, the lens being set to each diopter range without regard to focus of features shown by the lens;

capturing at least one image within each of the plurality of zones;

after capturing each image within each of the plurality of zones, displaying each image captured at each of the plurality of zones to a user;

prompting the user for a representative image; and receiving selection of the representative image from the user.

7. The method of claim 6, wherein the depth of field is from −10 diopters to +10 diopters.

8. The method of claim 7, wherein the depth of field is divided into 5 equal zones.

9. The method of claim 7, wherein the depth of field is divided into 10 zones.

10. The method of claim 6, wherein a light source is illuminated throughout the capture of each image in each zone.

* * * * *